US00PP21027P2

(12) United States Plant Patent
Perkins

(10) Patent No.: US PP21,027 P2
(45) Date of Patent: May 25, 2010

(54) ***SALVIA* PLANT NAMED 'MES PUR'**

(50) Latin Name: ***Salvia*×hybrid**
Varietal Denomination: Mes Pur

(75) Inventor: Ralph T. Perkins, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 56 days.

(21) Appl. No.: 12/313,157

(22) Filed: Nov. 18, 2008

(51) Int. Cl.
*A01H 5/00* (2006.01)

(52) U.S. Cl. ..... Plt./475

(58) Field of Classification Search ..... Plt./475
See application file for complete search history.

(56) References Cited

OTHER PUBLICATIONS

UPOV ROM GTITM Computer Database, GTI Jouve Retrieval Software 2009/04 Citation for 'Mes Pur'.*

* cited by examiner

*Primary Examiner*—Wendy C Haas
(74) *Attorney, Agent, or Firm*—S. Matthew Edwards

(57) ABSTRACT

A new *Salvia* plant named 'Mes Pur,' particularly distinguished by purple-violet flower color, upright, well branched, dense and bushy habit, medium green foliage and large sized flowers that are early flowering.

1 Drawing Sheet

Latin name of the genus and species of the plant claimed: *Salvia*×hybrid.

Varietal denomination: 'Mes Pur'.

BACKGROUND OF THE NEW PLANT

The present invention comprises a new *Salvia,* botanically known as *Salvia*×hybrid, and hereinafter referred to by the variety name 'Mes Pur'.

'Mes Pur' is a product of a planned breeding program. The new cultivar 'Mes Pur' has purple-violet flower color, upright, well branched, dense and bushy habit, medium green foliage and large sized flowers that are early flowering.

'Mes Pur' originated from an open pollination cross in a controlled breeding program in Gilroy, Calif. USA. The female parent was an unpatented, proprietary hybrid seedling *Salvia greggii*×(*S. microphylla*×*S. coaheuilensis*) identified as '82-3' with light purple color. '82-3' has fewer flowers, a taller and more open plant habit and darker foliage than 'Mes Pur.' The male parent of 'Mes Pur' was unknown.

'Mes Pur' was selected as one flowering plant within the progeny of the stated cross in September 2005 in a controlled environment in Gilroy, Calif. USA. The pollination took place in July 2004 and the seed sowing in May 2005.

The first act of asexual reproduction of 'Mes Pur' was accomplished when vegetative cuttings were taken from the initial selection in the September 2005 in a controlled environment in Gilroy, Calif. USA.

Horticultural examination of plants grown from cuttings of the plant initiated in September 2005 in Gilroy, Calif. USA, and continuing thereafter, has demonstrated that the combination of characteristics as herein disclosed for 'Mes Pur' are firmly fixed and are retained through successive generations of asexual reproduction.

'Mes Pur' has not been observed under all possible environmental conditions. The phenotype may vary significantly with variations in environment such as temperature, light intensity and day length.

A Plant Breeder's Right for this cultivar was applied for in Canada on Dec. 24, 2007. 'Mes Pur' has not been made publicly available more than one year prior to the filing of this application.

DESCRIPTION OF THE DRAWINGS

The accompanying photographic drawing shows typical flower and foliage characteristics of 'Mes Pur' with colors being as true as possible with an illustration of this type. The photographic drawing shows two flowering potted plants of the new variety and a close-up of the flowers, growing in a one gallon pot. This plant was grown and photographed in Gilroy, Calif. USA in April 2008. The plant was about 4 months old.

DETAILED BOTANICAL DESCRIPTION

The measurements were taken on plants growing in Gilroy, Calif. USA in April 2008. The plants were growing in gallon pots in a greenhouse trial. These plants were about 4-5 months old.

Color Chart used: Royal Horticultural Society Colour Chart (R.H.S.) 2001.

BRIEF SUMMARY OF INVENTION

The following observations, measurements, and comparisons describe plants grown Gilroy, Calif. USA. The following traits have been repeatedly observed and are determined to be basic characteristics of the new variety. The combination of these characteristics distinguishes this *Salvia* as a new and distinct variety.

TABLE 1

DIFFERENCES BETWEEN THE NEW CULTIVAR 'MES PUR' AND A SIMILAR VARIETY

| | 'Mes Pur' | 'Navajo Purple' (unpatented) |
|---|---|---|
| Floriferousness | More flowers | Fewer flowers |
| Foliage size | Larger | Smaller |
| Plant habit | More compact | Less compact |

Plant:

*Form, growth and habit.*—Upright, well branching, dense and bushy.

*Plant height.*—38-42 cm.
*Plant height (inflorescence included).*—47-50 cm.
*Plant width.*—45-50 cm.

Foliage:
*Type.*—Simple, opposite.
*Immature, leaf color, upper surface.*—RHS 146B.
*Lower surface.*—RHS 147A.
*Mature, leaf color, upper surface.*—Closest to RHS 147A.
*Lower surface.*—RHS 147A.
*Length.*—4.8-5.6 cm.
*Width.*—3.4-4.0 cm.
*Shape.*—Ovate.
*Base shape.*—Attenuate.
*Apex shape.*—Acute.
*Margin.*—Crenulate.
*Texture, upper surface.*—Hispid at margins; glandular hairs.
*Texture, lower surface.*—Hispid.
*Fragrant.*—Heavily "sage" like.
*Color of veins, upper surface.*—RHS 144B.
*Color of veins, lower surface.*—RHS 144B.
*Petioles color.*—RHS 144B.
*Petioles length.*—0.9-1.1 cm.
*Diameter of petiole.*—0.15 cm.
*Texture.*—Hispid.

Stem:
*Number of main branches per plant.*—2-3.
*Number of leaves per stem.*—14-20.
*Color of stem.*—Between RHS 144A and B.
*Length of stem.*—29-32 cm.
*Diameter.*—0.3 cm.
*Length of internodes.*—4.5-5 cm.
*Texture.*—Hispid; muriculate.

Inflorescence:
*Type.*—Terminal raceme.
*Blooming habit.*—Flowers continuously from spring through the fall.
*Number of racemes per plant.*—40-50.
*Duration of flowering.*—Continuous flowering throughout the summer.
*Color of peduncle.*—RHS N187A to B.
*Length of peduncle.*—9-14 cm.
*Peduncle diameter.*—0.3 cm.
*Texture.*—Hispid; many glandular hairs.
*Color of pedicel.*—Slight hue of RHS N187A.
*Length of pedicel.*—0.4 cm.
*Diameter of pedicel.*—0.05 cm.
*Texture.*—Few hispid; many glandular hairs.

Corolla:
*Form.*—Single: bilabiate; with one upper lip, and one lower lip with three lobes consisting one a mid-lobe and 2 small lateral lobes; fused at base; upper lip wraps around the pistil.
*Lastingness of individual bloom on the plant.*—4-6 days.
*Fragrance.*—"Sage" like.
*Immature florets.*—
*General color, upper surface.*—RHS N81A but darker.
*Lower surface.*—Closest to RHS N82D but greyer.
*Mature florets.*—
*Vertical height of floret.*—1.8-2.0 cm.
*Horizontal width of floret.*—1.7-1.8 cm.
*Depth of floret.*—2.3-2.5 cm.
*Color upper lip, upper surface.*—Closest to RHS N80A but appears brighter because of the RHS N81A color of the villous hairs.
*Color upper lip, lower surface.*—Closest to RHS N82D but greyer.
*Length of upper lip.*—0.8-0.9 cm.
*Width of upper lip.*—0.3 cm.
*Shape.*—Obovate.
*Apex shape.*—Obtuse.
*Margin.*—Entire.
*Texture, outer surface.*—Hispid; short villous hairs of RHS N81A at the apex.
*Inner surface.*—Glabrous.
*Color lower lip, mid-lobe, upper surface.*—RHS N80A; small blotch of RHS N82D to RHS N155B basally.
*Color lower lip, mid-lobe, lower surface.*—Closest to RHS N82D but greyer.
*Length of lower lip, mid-lobe.*—1.5-1.6 cm.
*Width of lower lip, mid-lobe.*—1.1-1.2 cm.
*Shape.*—Obovate.
*Apex shape.*—Emarginate.
*Margin.*—Entire.
*Texture, upper surface.*—Papillose.
*Lower surface.*—Glabrous.
*Color lower lip, lateral lobe, upper surface.*—RHS N80A.
*Color lower lip, lateral lobe, lower surface.*—Closest to RHS N82D but lighter.
*Length of lower lip, lateral lobe.*—0.7-0.8 cm.
*Width of lower lip, lateral lobe.*—0.3-0.35 cm.
*Petal shape.*—Oblong.
*Apex shape.*—Obtuse.
*Margin.*—Entire.
*Texture, upper surface.*—Papillose.
*Lower surface.*—Glabrous.
*Corolla, color, outer surface.*—RHS N80A.
*Inner surface.*—RHS N82D but greyer.
*Length of corolla.*—1.2-1.3 cm.
*Width of corolla.*—0.4-0.5 cm at the widest portion.
*Texture, outer upper surface.*—Glandular hairs.
*Texture, outer lower surface.*—Glabrous.
*Texture, inner surfaces.*—Glabrous.

Bud (just before opening):
*Color.*—RHS 79A.
*Length.*—1.2-1.4 cm.
*Width.*—0.3-0.5 cm.
*Shape.*—Tubular to oblong.

Calyx:
*Number of sepals.*—2, fused into a tube form.
*Color of sepals, upper surface.*—RHS 148A basally; RHS N187A mid-veins; RHS 187B between the mid-veins.
*Inner surface.*—RHS 193A.
*Length of sepals.*—1.3-1.4 cm.
*Width of sepals.*—0.3-0.4 cm.
*Sepal shape.*—Broadly linear.
*Apex shape.*—Acute.
*Margin.*—Entire.
*Texture, outer surface.*—Hispid; glandular hairs.
*Inner surface.*—Glabrous.

Reproductive organs:
*Pistil.*—1.
*Length.*—2.7-2.8 cm.
*Style color.*—RHS N155B.
*Style length.*—2.4-2.6 cm.

*Stigma color.*—RHS N82B.
*Stamens.*—2.
*Color of filaments.*—RHS N155B but whiter.
*Anther color.*—RHS 167D.
*Anther length.*—0.1-0.2 cm.
*Color of pollen.*—RHS 17B.
*Pollen amount.*—Moderate.
*Fertility/seed set.*—Not observed on this hybrid.

Disease/pest resistance: Disease resistance or susceptibility has not been observed on this hybrid.

What is claimed is:

1. A new and distinct variety of *Salvia* plant named 'Mes Pur,' substantially as illustrated and described herein.

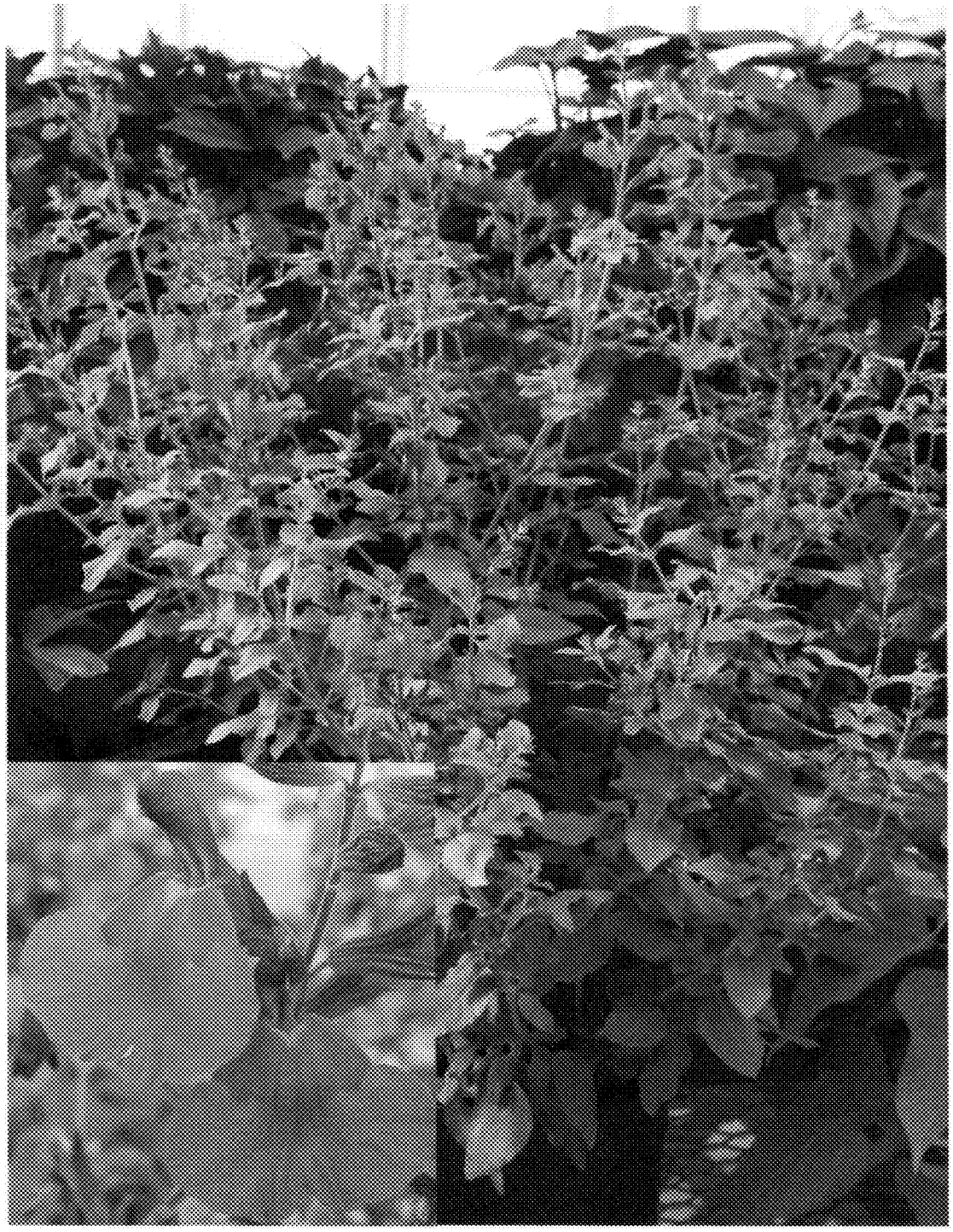

* * * * *